US009939400B1

United States Patent
Gozzini et al.

(10) Patent No.: US 9,939,400 B1
(45) Date of Patent: Apr. 10, 2018

(54) FIXED PATTERN NOISE COMPENSATION TECHNIQUES FOR CAPACITIVE FINGERPRINT SENSORS

(71) Applicant: Apple Inc., Cupertino, CA (US)

(72) Inventors: Giovanni Gozzini, Cupertino, CA (US); Gordon S. Franza, Cupertino, CA (US); Jean-Marie Bussat, Cupertino, CA (US); Patrick J. Landy, Cupertino, CA (US)

(73) Assignee: Apple Inc., Cupertino, CA (US)

( * ) Notice: Subject to any disclaimer, the term of this patent is extended or adjusted under 35 U.S.C. 154(b) by 375 days.

(21) Appl. No.: 14/481,534

(22) Filed: Sep. 9, 2014

Related U.S. Application Data

(60) Provisional application No. 61/875,624, filed on Sep. 9, 2013.

(51) Int. Cl.
*G01N 27/22* (2006.01)
*G06K 9/00* (2006.01)

(52) U.S. Cl.
CPC ......... *G01N 27/221* (2013.01); *G06K 9/0002* (2013.01)

(58) Field of Classification Search
USPC ........ 324/663, 658, 686; 382/115, 124, 103; 345/173–178; 348/E5.091, E3.021; 257/E27.132; 702/104
See application file for complete search history.

(56) References Cited

U.S. PATENT DOCUMENTS

| | | | |
|---|---|---|---|
| 5,877,715 A * | 3/1999 | Gowda | H03M 1/1023 341/118 |
| 6,330,345 B1 | 12/2001 | Russo et al. | |
| 6,556,935 B2 | 4/2003 | Morimura | |
| 6,766,040 B1 | 7/2004 | Catalano et al. | |
| 6,990,219 B2 | 1/2006 | Morimura et al. | |
| 7,072,523 B2 | 7/2006 | Bolle et al. | |
| 7,102,673 B2 | 9/2006 | Kimura | |
| 7,358,514 B2 | 4/2008 | Setlak et al. | |
| 7,813,534 B2 | 10/2010 | Ryhanen et al. | |

(Continued)

OTHER PUBLICATIONS

U.S. Appl. No. 13/947,572, filed Jul. 22, 2013, Gozzini et al.
U.S. Appl. No. 13/948,097, filed Jul. 22, 2013, Gozzini et al.
U.S. Appl. No. 14/020,886, filed Sep. 8, 2013, Breznicky.

*Primary Examiner* — Daniel Miller
*Assistant Examiner* — Nasima Monsur
(74) *Attorney, Agent, or Firm* — Brownstein Hyatt Farber Schreck, LLP

(57) ABSTRACT

A capacitive fingerprint sensor includes an array of capacitive sensing elements, readout circuitry electrically coupled to the array of capacitive sensing elements, a block first digital to analog converter (DAC), at least one second DAC, and at least one summing junction electrically coupled to the readout circuitry, the first DAC, and the at least one second DAC. The readout circuitry is adapted to read out pixel voltages from a group of each block of capacitive sensing elements. The first DAC is adapted to provide a block baseline voltage for each block of capacitive sensing elements. The second DAC is adapted to provide a pixel baseline voltage difference for one capacitive sensing element of each group of each block. The summing junction is adapted to subtract the received block baseline voltage and the received pixel baseline voltage difference from the corresponding pixel voltage of each row of each block.

23 Claims, 4 Drawing Sheets

(56) References Cited

U.S. PATENT DOCUMENTS

| | | |
|---|---|---|
| 7,965,874 B2 | 6/2011 | Abiko et al. |
| 8,098,906 B2 | 1/2012 | Shuckers et al. |
| 8,622,302 B2 | 1/2014 | Olmstead |
| 8,654,571 B2 | 2/2014 | John et al. |
| 9,195,879 B1 | 11/2015 | Du |
| 9,224,030 B2 | 12/2015 | Du et al. |
| 2001/0050728 A1* | 12/2001 | Edwards .............. G09G 3/3648 349/33 |
| 2009/0231479 A1* | 9/2009 | Zarnowski ............ H03M 1/123 348/302 |
| 2009/0274343 A1 | 11/2009 | Clarke |
| 2010/0174914 A1 | 7/2010 | Shafir |
| 2012/0300992 A1 | 11/2012 | Ivanov et al. |
| 2013/0287274 A1* | 10/2013 | Shi .......................... G06F 3/044 382/124 |
| 2013/0315451 A1 | 11/2013 | Franza |
| 2015/0022670 A1 | 1/2015 | Gozzini et al. |
| 2015/0023571 A1 | 1/2015 | Gozzini et al. |
| 2015/0071502 A1 | 3/2015 | Breznicky |

\* cited by examiner

FIXED PATTERN NOISE COMPENSATION TECHNIQUES FOR CAPACITIVE FINGERPRINT SENSORS

CROSS-REFERENCE TO RELATED APPLICATION

This application claims the benefit under 35 U.S.C. § 119(e) of U.S. Provisional Patent Application No. 61/875,624, filed Sep. 9, 2013, entitled "Fixed Pattern Noise Compensation Techniques For Capacitive Fingerprint Sensors," the entirety of which is incorporated herein by reference as if fully disclosed herein.

TECHNICAL FIELD

This application relates generally to reducing fixed pattern noise in capacitive fingerprint sensing systems, and more particularly to the use of digital to analog converters (DACs) to compensate for fixed pattern noise in capacitive sensing systems.

BACKGROUND

There is considerable interest in providing consumer electronic devices, including smart phones, computers, electronic tablets, and so on, with various means of securing information stored on these devices. Biometric security systems, such as fingerprint recognition systems, are one approach to providing these security features. These systems may not require memorization, or the use of any other device by the user, as security may be based on unique features of the user. They also provide the potential advantage being difficult to 'crack' for the same reasons.

Fingerprint recognition systems generally collect fingerprint images and compare those images against a database of known fingerprint information. For example, after a set of fingerprint images for a known authorized user is collected and processed, a user wishing access can be authorized by collecting one or more fingerprint images for that accessing user and comparing these collected images against known fingerprint information for the authorized user. One example of a fingerprint recognition system uses capacitive sensing elements to detect fingerprint images for collection. Such sensors are able to detect electric field differences between ridges and valleys of the fingerprint of a finger in contact with a contact surface of the consumer electronic device adapted for this purpose by measuring charge accumulated by the capacitive sensing elements.

In an example capacitive fingerprint sensor, these electric field differences are small compared to the total electric fields being measured and the charge accumulated is proportional to the total electric field. However, the signal produced by the capacitive sensing elements in such an example capacitive fingerprint sensor may include a relatively large fixed pattern signal that is based on the baseline carrier level accumulated by the capacitive sensing elements, even in the absence of a finger to image. This baseline signal is not based on the electric field differences of interest, but rather on parameters of the capacitive sensing elements. Because the electric field differences of interest are very small, typically the signals detected by the capacitive sensing elements are amplified. However, amplifying the signals not only amplifies the difference signal of interest, but also amplifies the baseline signal of the capacitive sensing elements as well. Thus, any noise that is proportional to overall signal level generated during amplification may lead to a large fixed pattern noise component and significantly impact the signal to noise ratio of the fingerprint data.

The effectiveness of biometric security systems may be affected by the accuracy with which the unique biometric data on which they are based is able to be detected. In the case of fingerprint identification systems, this means that improved signal to noise ratios for detection of fingerprint data may lead to improved security for the secured device. Therefore, improving signal to noise ratios for detection of finger print data may be a significant issue in such systems.

SUMMARY

One example embodiment, as described herein, is a capacitive fingerprint sensor, including an array of capacitive sensing elements. The array of capacitive sensing elements includes multiple blocks of capacitive sensing elements. The capacitive fingerprint sensor also includes: readout circuitry electrically coupled to the array of capacitive sensing elements; a block first digital to analog converter (DAC); at least one second DACs; and at least one summing junctions. The readout circuitry is adapted to read out pixel voltages from a group of each block of capacitive sensing elements. The first DAC is adapted to provide a block baseline voltage for each block of capacitive sensing elements. The at least one second DAC is adapted to provide a pixel baseline voltage difference for one capacitive sensing element of each group of each block. The at least one summing junction is electrically coupled to the readout circuitry, the first DAC, and the at least one second DACs. The at least one summing junction is adapted to subtract the received block baseline voltage and the received pixel baseline voltage difference from the corresponding pixel voltage of each row of each block.

Another example embodiment, as described herein, is a method for reducing fixed pattern noise (FPN) in a series of pixel voltages read out from a block of capacitive sensing elements. The series of pixel voltages is received. A block baseline voltage corresponding to the block of capacitive sensing elements is determined and pixel baseline voltage differences, each pixel baseline voltage difference corresponding one capacitive sensing element of the block, are determined. The block baseline voltage and the corresponding pixel baseline voltage difference are serially subtracted from each pixel voltage to provide a series of reduced FPN pixel voltages.

A further example embodiment, as described herein, is a capacitive fingerprint sensor, including an array of capacitive sensing elements. The array of capacitive sensing elements includes multiple blocks of capacitive sensing elements. The capacitive fingerprint sensor also includes: readout circuitry electrically coupled to the array of capacitive sensing elements; a first DAC; at least one second DAC; and at least one summing junction. The readout circuitry is adapted to read out pixel voltages from the capacitive sensing elements from a group of each block. The first DAC is adapted to serially provide a block baseline carrier level for each block of the capacitive sensing elements. The at least one second DAC is coupled to the first DAC to serially receive the block baseline carrier levels. The at least one second DAC is adapted to serially add a pixel baseline carrier level difference for a capacitive sensing element of the group of each block to the block baseline carrier level of the block to generate a pixel baseline carrier level for the corresponding capacitive sensing element. The at least one summing junction is capacitively coupled to the readout circuitry to receive pixel voltages. Each pixel voltage is proportional to the pixel charge of a capacitive sensing element. The at least one summing junction is also capacitively coupled to the at least one second DAC to receive pixel baseline voltages. Each pixel baseline voltage is proportional to the pixel baseline carrier level of a corresponding capacitive sensing element. The at least one summing junction is adapted to serially subtract the corresponding pixel baseline voltage from each pixel voltage to provide a series of reduced FPN pixel voltages.

While multiple embodiments are disclosed, including variations thereof, still other embodiments of the present disclosure will become apparent to those skilled in the art from the following detailed description, which shows and describes illustrative embodiments of the disclosure. As will be realized, the disclosure is capable of modifications in various obvious aspects, all without departing from the spirit and scope of the present disclosure. Accordingly, the drawings and detailed description are to be regarded as illustrative in nature and not restrictive.

BRIEF DESCRIPTION OF THE DRAWINGS

While the specification concludes with claims particularly pointing out and distinctly claiming the subject matter that is regarded as forming the present disclosure, it is believed that the embodiments are best understood from the following detailed description when read in connection with the accompanying drawing. It should be understood that the various features of the drawing may not be to scale. Likewise, the dimensions of the various features may be altered for clarity. Included in the drawings and/or illustrations are the following figures:

DETAILED DESCRIPTION

As discussed above, there is significant interest in including biometric security systems, such as capacitive fingerprint sensors in various consumer electronics devices. However, the accuracy of example capacitive fingerprint sensors may be affected by fixed pattern noise (FPN) components that may be large relative to the signal of interest in these example sensors.

Example embodiments described herein may reduce the fixed pattern signal generated by the array of capacitive sensing elements in an example capacitive fingerprint sensor at the front end of processing the fingerprint data, thus potentially significantly reducing FPN in the example sensor and thereby improving the signal to noise ratio of the processed fingerprint data. This improved signal to noise ratio may lead to the ability to detect improved quality fingerprint images, which can increase the accuracy of biometric security systems based on capacitive fingerprint sensors.

Figure 1A:
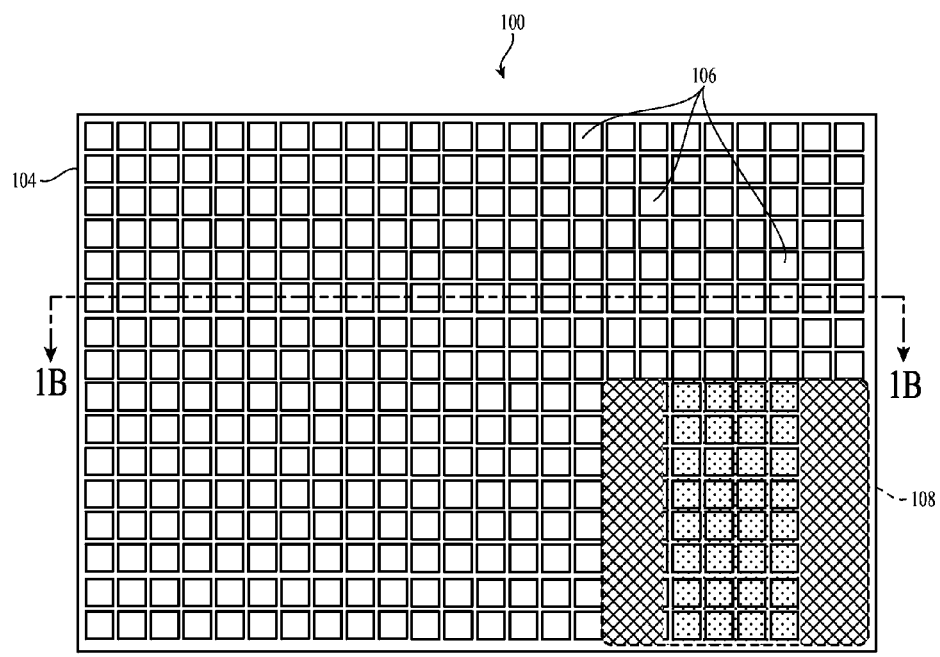
FIG. 1A is a top plan drawing of an example capacitive sensor array.
Figure 1B:
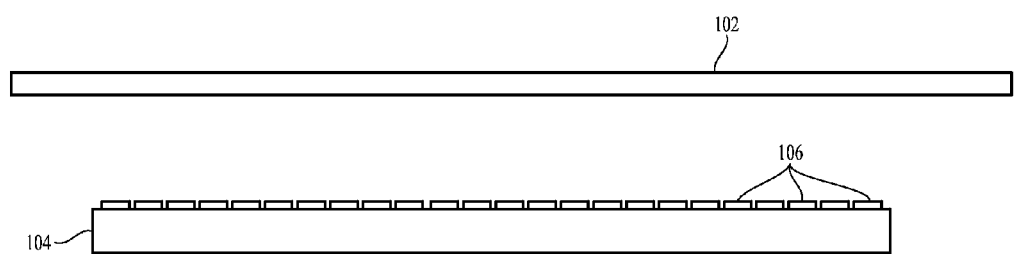
FIG. 1B is a cross-sectional view of the example capacitive sensor array of FIG. 1A taken along line 1B-1B.

As discussed above, the capacitive sensing elements in certain example capacitive fingerprint sensors operate by accumulating charge within the capacitive sensing element. FIGS. 1A and 1B illustrate one example array of capacitive sensing elements that may be used with example embodiments described herein. In the illustrated array of capacitive sensing elements 100, the individual capacitive sensing elements are defined by electrodes 106 which are formed on substrate 104. The electrodes 106 may be individually formed as discrete electrodes in certain embodiments.

As a non-limiting alternative, each electrode 106 may be formed at the intersection of a drive line and a sense line (not shown). In either embodiment, the electrodes 106 may be excited. A voltage (e.g., charge) may be present within any given electrode and vary as a result of the excitation. The presence or absence of a conductive region (such as human skin) above the electrode, the distance to such a conductive region, and so on, can vary the voltage present at one or more electrodes. Once charge is accumulated within the electrode, it may be read out (either through a unique connection for each capacitive sensing element or through the aforementioned sense lines, depending on the physical structure). This raw fingerprint data then undergoes a signal processing procedure that may include amplification, filtering, noise reduction, and/or other signal processing steps to be performed on the fingerprint data. The measured variances in charge upon each electrode may be used to assemble a map of a fingerprint or other conductive surface forming the aforementioned conductive regions.

In the absence of a finger or other conductive material being in contact with contact surface 102, the contact surface 102 may act as a common electrode for all of the capacitive sensing elements. Although not shown in FIG. 1B, the contact surface 102 and the substrate 104 may be positioned at a fixed distance from one another. Typically, this fixed distance does not change or changes only minimally with time. In some embodiments, the array 100 may abut a surface of the contact surface 102.

In addition to depending on certain external factors, such as the fingerprint pattern of a finger in contact with the contact surface 102, the charge accumulated in each capacitive sensing element depends on various parameters specific to each capacitive sensing element, including any variability in the electrode 106 associated with the capacitive sensing element, the position of the capacitive sensing element within the array of capacitive sensing elements, and possibly one or more factors relating to the electronic device that is housing the array of capacitive sensing elements 100. Thus, even in the absence of a fingerprint to be detected by the array of capacitive sensing elements 100, each capacitive sensing element may accumulate a different amount of charge during a measurement cycle. The amount of charge accumulated by each individual capacitive sensing element in the absence of anything to be detected is typically relatively stable, for any given bias level (i.e. a relative voltage level applied to the capacitive sensing elements during the accumulation portion of a measurement cycle of the capacitive fingerprint sensor), and thus may be seen as a fixed pattern of baseline charge accumulation across the array of capacitive sensing elements 100. This fixed pattern baseline charge accumulation may be measured and stored during characterization of the array of capacitive sensing elements at one or more bias levels. Alternatively, it may be measured during initialization of the fingerprint sensor, before a finger has been place on the contact surface 102. In many cases, the baseline charge accumulation at any given electrode 106 may be significantly larger than the charge accumulation representing the fingerprint data of interest.

Signal amplification often introduces noise that is proportionate to the signal amplitude. Therefore, amplifying excess (non-data) signals, such as carrier signals, may cause desired data, such as the data representing a fingerprint feature or other biometric feature, to be difficult to detect. This issue is exacerbated when the excess carrier signal exceeds the signal of interest. As noted above, the effectiveness of biometric security systems depends on the accuracy with which the unique biometric data on which they are based can be detected. For capacitive fingerprint sensor systems, this means that improved signal to noise ratios for fingerprint data collection may lead to improved security for the secured device. Therefore, improving signal to noise ratios for detection of finger print data may be a significant issue in such systems.

To address this issue, example embodiments described herein may reduce the fixed pattern signal associated with the baseline charge accumulation of capacitive sensing elements in example array 100. One approach may be to reduce the signal from each capacitive sensing element by a predetermined amount. This approach may provide for some improvement of the signal to noise ratio for processed fingerprint data by removing a significant portion of the baseline noise. However, it may not address certain artifacts in the fixed pattern of the baseline charge accumulation.

Another example approach may be to provide a variable signal reduction specific to each capacitive sensing element. Such an approach may reduce the fixed pattern noise (FPN) associated with an example capacitive fingerprint sensor, and can also reduce artifacts in the data due to the fixed pattern baseline charge accumulation of the example array. Example embodiments described herein include various means of implementing this approach to reduce the fixed pattern signal (and thus FPN) associated with the baseline charge accumulation of capacitive sensing elements in example array 100.

These example embodiments may include the use of digital to analog converters (DACs) to provide baseline signals that are approximately equal to the fixed pattern signals of the array of capacitive sensing elements. DACs may provide reliable and low noise signal levels. The more input bits that a DACs has, the finer each step in signal may be for a set range of analog output values; however, a smaller analog output range may allow a DAC with fewer input bits to achieve a small step size as well.

These baseline signals generated by the DAC are then subtracted from the measured fingerprint data signal received from the capacitive sensing elements of array 100 at an early point in the signal processing procedure using a summing junction. Subtracting these baseline signals from the measured fingerprint data reduces the overall level of the fingerprint data signal, but does not reduce the signal variations that contain the fingerprint information of interest. Thus, the fingerprint data signal that is amplified during further amplification steps of the signal processing procedure may contain a higher percentage of the fingerprint information of interest compared to background, thereby reducing the noise associated with amplifying this background, i.e. reducing the fixed pattern noise.

As noted above, reducing the fixed pattern baseline signal near the front end of the signal processing may provide greater signal to noise ratio improvement. Therefore, it is contemplated that example embodiments described herein may utilize circuitry fabricated on the sensor array chip itself to allow implementation within the initial signal processing steps. However, it is also contemplated that example embodiments described herein may also be realized with some or all of the circuitry of these embodiments formed on separate chips and/or separate substrates of a stacked chip configuration.

FIG. 1A illustrates example 8×8 capacitive sensing element block 108 in the array of capacitive sensing elements 100. Many capacitive fingerprint sensors include readout circuits designed to read out accumulated charge in blocks of capacitive sensing elements. In some embodiments, the readout circuits may read out the accumulate charge one row of a block at a time, possibly including a parallel readout line for each column of the block. These example readout circuits provide a model for implementation of a two stage DAC approach to reducing the fixed pattern signal (and thus FPN) from capacitive fingerprint sensors.

One approach used by example embodiments described herein is to employ a two stage system of DACs for generating the baseline signals. A first stage DAC may have a larger analog output range to provide a baseline signal level for a block of the array of capacitive sensing elements, while a second stage DAC may have a smaller analog output range to provide fine baseline signal corrections for each sensing element. Selection of the number of bits of the digital inputs of the DAC stages may further tailor the tuning of these baseline signal corrections. For example, if the first stage and second stage DACs have the same number of digital input bits, then the ratio between the step sizes of the first stage DAC and a second stage DAC is equal to the ratio of their output ranges. Alternatively, the first stage DAC may have both a digital input with a larger number of bits (for example, 8 bits or more) and a larger analog output range, while a second stage DAC may have a digital input with a smaller number of bits (for example, less than 8 bits) but also a smaller analog output range. Through selecting the input bits and output ranges, the first DAC, which may take up significant chip space, may set a coarse baseline signal correction level, while the second, smaller, DAC may provide a finer correction.

Often, the readout circuitry of an example capacitive fingerprint sensor may include a separate parallel readout line for each column in a block. As noted, the first stage DAC may be used to provide a baseline signal level for a block of the array of capacitive sensing elements. However, for the second stage, an example embodiment described herein may include one smaller bit range DAC coupled to each parallel line of the readout circuitry. These second stage DACs may provide fine baseline signal corrections for each sensing element in the corresponding column. The example embodiments described below use one parallel readout line and associated second stage DAC (i.e. parallel signal processing line) for each column of a block of capacitive sensing elements. It may be understood by one skilled in the art that these example embodiments are merely illustrative and that other example embodiments including fewer parallel signal processing lines, or even a single signal processing line may be used as well.

Figure 2:
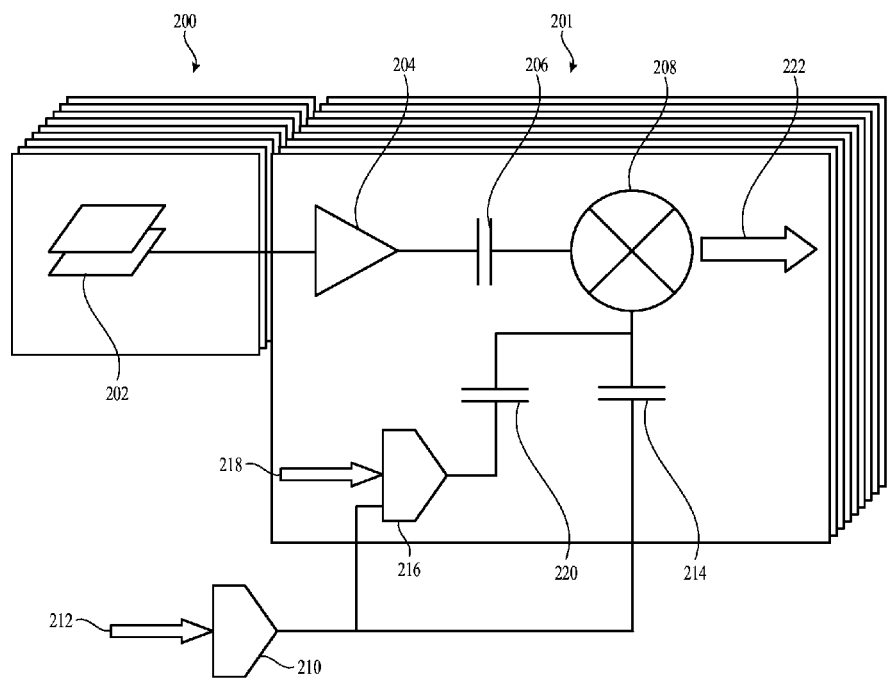
FIG. 2 is a schematic block diagram of an example capacitive sensor array and readout circuitry and fixed pattern noise (FPN) reduction circuitry.

FIG. 2 illustrates an example capacitive fingerprint sensor that incorporates a two stage DAC approach to reducing FPN. The example capacitive fingerprint sensor includes an array of capacitive sensing elements 202 and associated readout and FPN reduction circuitry. The array of capacitive sensing elements forms a plurality of blocks. Each of these blocks has a number of rows and a number of columns of capacitive sensing elements. The number of rows and columns may be eight, as in the example block 108 of array 100 of FIG. 1A. Other embodiments can include a different number of rows and columns in a block (a number other than eight). Additionally or alternatively, the number of rows and/or columns in a block does not have to be the same number(s) in each block.

FIG. 2 illustrates only one row 200 of one block of the array of capacitive sensing elements 202 to simplify the drawing and clarify features of the example embodiments. As illustrated, row 200 includes eight capacitive sensing elements 202 and eight parallel signal processing circuitry 201, shown graphically by the stacked boxes in this figure. This selection is merely illustrative and is not intended as limiting. In these example embodiments, accumulated pixel charges are read out one row of one block at a time and the readout circuitry, which is part of parallel signal processing circuitry 201, includes one parallel line for each column of the block, e.g. eight lines in the example of FIG. 2.

This example embodiment includes a two stage DAC system for FPN reduction. The first stage of this example two stage DAC system, referred to hereinafter as the "block FPN DAC," includes a single first stage DAC 210 and block FPN DAC coupling capacitors 214. The second stage of this example two stage DAC system, referred to hereinafter as the "pixel FPN DAC," includes second stage DACs 216 and corresponding pixel FPN DAC coupling capacitors 220. It is noted that although first stage DAC 210 is not part of any one of line of parallel signal processing circuitry 201, the block FPN DAC, including first stage DAC 210 and block FPN DAC coupling capacitors 214 is part of the signal processing circuitry of the example capacitive fingerprint sensor of FIG. 2.

Although the disclosure generally discusses the use of coupling capacitors, it should be appreciated that other electrical circuit elements may be used in place of coupling capacitors, as known to those of ordinary skill in the art.

Parallel signal processing circuitry 201 includes one parallel line of circuitry for each column of a block of the array of capacitive sensing elements 202, shown graphically by the stacked boxes in FIG. 2. Each parallel line of parallel signal processing circuitry 201 includes one line of the readout circuitry, which includes preamplifier 204 and readout coupling capacitor 206. The input of preamplifier 204 is serially coupled to the capacitive sensing elements in one column of each block of the array of capacitive sensing elements by switching circuitry (not shown). Each parallel line of parallel signal processing circuitry 201 also includes one second stage DAC 216, one block FPN DAC coupling capacitor 214, and one pixel FPN DAC coupling capacitor 220, as well as summing junction 208. Inputs of each summing junction 208 are capacitively coupled to the outputs of a corresponding preamplifier 204, corresponding second stage DAC 216, and first stage DAC 210, by corresponding readout coupling capacitor 206, corresponding pixel FPN DAC coupling capacitor 220, and corresponding block FPN DAC coupling capacitor 214, respectively. Arrow 222 represents the subseries of FPN reduced signals generated by summing junction 208, which is transmitted to further signal processing circuitry (not shown) to complete signal processing of the fingerprint image data. Each of these subseries 222 of FPN reduced signals includes voltage levels representative of the variations in charge accumulated by capacitive sensing elements in one column of each block of the array of capacitive sensing elements. These subseries may be combined for further signal processing steps, such as amplification and filtering, or they may be processed in parallel and combined later. In some embodiments, the preamplifiers may be omitted, and/or signal correction may occur at a different part of the circuitry.

In this example embodiment, the readout circuitry (including preamplifiers 204 and readout coupling capacitors 206) is electrically coupled to the array of capacitive sensing elements, as well as to summing junctions 208. Each capacitive sensing element 202 of the array of capacitive sensing elements stores a pixel charge during a measurement period prior to read out. The readout circuitry read out the pixel charges from each block of capacitive sensing elements 202 one row at a time. As it is read out, the pixel charge from one column of capacitive sensing elements 202 is coupled to a corresponding parallel preamplifier 204 to be amplified. The amplified pixel charge is used to charge corresponding readout coupling capacitor 206 to produce a pixel voltage, which is applied to the corresponding summing junction 208.

Block FPN DAC (including first stage DAC 210 and block FPN DAC coupling capacitors 214) provide a block baseline voltage for each block of capacitive sensing elements. In this example embodiment, first stage DAC 210 generates a block baseline charge for each block of the capacitive sensing elements based on a corresponding digital block baseline value. First stage DAC input 212 includes the digital block baseline value as well as a latching signal to synchronize first stage DAC 210 with the readout circuitry. The digital block baseline values may be calculated in various ways from the measured baseline carrier levels of the capacitive sensing elements; however, they are scaled based on the number of input bits of first stage DAC 210, so that all of the digital block baseline values are within the input range of first stage DAC 210, i.e. if first stage DAC 210 has G input bits, the digital block baseline values may range from 0 to $2^G-1$. For example, if first stage DAC 210 has 10 input bits, then the maximum digital block baseline value would be $2^{10}-1$, or 1023.

Based on the digital block baseline value applied to the input of first stage DAC 210, first stage DAC 210 generates an analog block baseline charge. The block baseline charge generated by first stage DAC 210 is used to charge block FPN DAC coupling capacitors 214 and produce the block baseline voltage for each block of capacitive sensing elements. Each block FPN DAC coupling capacitor 214 is coupled to one summing junctions 208 to apply the block baseline voltage to that summing junction. The block baseline charge is also coupled to an input of each second stage DAC 216 for use in calculating a pixel baseline voltage difference for each capacitive sensing element.

Each parallel line of parallel signal processing circuitry 201 includes a pixel FPN DAC (including a second stage DAC 216 and a pixel FPN DAC coupling capacitor 220) that provides a pixel baseline voltage difference for each capacitive sensing element in corresponding columns of blocks of the array of capacitive sensing elements. In this example embodiment, second stage DACs 216 generates a pixel baseline charge difference, i.e. the difference (approximately) between the measured baseline carrier level of a capacitive sensing element and the block baseline charge generated by first stage DAC 210, for each capacitive sensing element. Second stage DACs 216 generates analog pixel baseline charge difference based on a corresponding digital pixel baseline difference value.

Second stage DAC input 218 includes the digital pixel baseline difference value as well as a latching signal to synchronize second stage DAC 216 with the readout circuitry. The digital pixel baseline difference values are calculated based on the block baseline charge generated by first stage DAC 210. Additionally, the digital pixel baseline difference values are scaled based on the number of input bits of second stage DAC 216, so that all of the digital pixel baseline difference values are within the input range of second stage DAC 216. Specific examples for calculating both the digital block baseline values and digital pixel baseline difference values are described in detail below.

The pixel baseline charge difference generated by each second stage DAC 216 is used to charge the corresponding pixel FPN DAC coupling capacitor 220 and produce the pixel baseline voltage difference for the corresponding capacitive sensing element. Each pixel FPN DAC coupling capacitor 220 is coupled to one summing junction 208 to apply the pixel baseline voltage difference to that summing junction.

Each summing junction 208 includes circuitry adapted to subtract the received block baseline voltage and the received pixel baseline voltage difference from the corresponding pixel voltage and produce a subseries of reduced FPN pixel voltages 222. The amplitude of the reduced FPN pixel voltages are typically significantly lower than the pixel voltages applied to summing junctions 208. However, because only portions of the pixel voltage due to baseline charge accumulation (i.e. the fixed pattern signal) have been subtracted by summing junctions 208, an increased percentage of each reduced FPN pixel voltage may be due to fingerprint image data, rather than due to the baseline signal. Thus, these example embodiments may allow further signal processing stages to amplify the fingerprint image data without significant deterioration of the signal to noise ratio.

It is contemplated that the following specific examples of methods to derive the various baseline parameters used in embodiments of the capacitive fingerprint sensor of FIG. 2 may further illuminate some of its features. These specific examples are presented as merely illustrative and are not intended as limiting.

In each of these example embodiments, the parameters of each parallel preamplifier stage 204 and corresponding readout coupling capacitor 206 may be selected such that the readout circuitry has a predetermined readout gain from pixel charge accumulated by capacitive sensing element 202 and the pixel voltage applied to summing junction 208.

In one example embodiment, the baseline carrier levels of the capacitive sensing elements may be determined by measuring the carrier accumulation with no finger present. The average of the baseline carrier levels of the capacitive sensing elements of each block may be calculated. The digital block baseline value for each block may be an integer selected based on the corresponding block average baseline carrier levels. As noted above, the digital block baseline values for all of the blocks are scaled so that they all fall within the input bit range of first stage DAC 210. In one example embodiment, this may be accomplished by dividing the highest input value of first stage DAC 210 (the highest binary number within the bit range of the digital input) by the maximum block average baseline carrier level to determine a block scaling factor. The digital block baseline value for each block may then be selected to be approximately equal to (i.e. the closest binary value to) the corresponding block average baseline carrier levels times the block scaling factor.

Generally, it should be appreciated that a median, mean, or other suitable metric may be used in place of any average discussed herein.

In this example embodiment, each digital pixel baseline difference value is an integer selected based on the block average baseline carrier levels as well, or more specifically on the baseline carrier level of the corresponding capacitive sensing element minus the corresponding block average baseline carrier level, i.e. the baseline carrier deviation. Similarly to the selection of the digital block baseline values described above, a scaling factor, in this case the pixel scaling factor, may be used to map the baseline carrier deviations onto the input range of each second stage DAC 216 to select the digital pixel baseline difference values. It is noted that this example embodiment yields both positive and negative baseline carrier deviation, and thus, both positive and negative digital pixel baseline difference values. Thus, the pixel scaling factor may be calculated by dividing highest input value of second stage DACs 216 by the highest absolute value of any of the baseline carrier deviations. Each digital pixel baseline difference value is selected to be approximately equal to the baseline carrier deviation multiplied by the pixel scaling factor. In this example embodiment, second stage DACs 216 may be selected such that both their input ranges and their output ranges may include negative values and may be selected to be centered on 0.

Further, in this example embodiment, the analog output range of first stage DAC 210 and the capacitance of block FPN DAC coupling capacitors 214 may be chosen such that there is a predetermined block FPN DAC gain between the block average baseline carrier levels and the corresponding block baseline voltage applied to summing junctions 208 (i.e., for each block, the block baseline voltage that is applied to summing junctions 208 equals the block average baseline carrier level of the block times a predetermined scaling factor, the block FPN DAC gain, which is the same). Additionally, the analog output ranges of second stage DACs 216 and the capacitance of pixel FPN DAC coupling capacitors 220 may be chosen such that there is a predetermined pixel FPN DAC gain between the baseline carrier deviations and the corresponding pixel baseline voltage differences applied to summing junctions 208 (i.e., for each pixel, the pixel baseline voltage difference that is applied to summing junctions 208 equals the baseline carrier deviation of the pixel times a predetermined scaling factor, the pixel FPN DAC gain, which is the same).

In another example embodiment, the baseline carrier levels of the capacitive sensing elements may be determined by measuring the carrier accumulation with no finger present. In this example embodiment, the digital block baseline values may be based on the lowest baseline carrier level of the capacitive sensing elements of each block, instead of the average baseline carrier level. As noted above, the digital block baseline values for all of the blocks are scaled so that they all fall within the input bit range of first stage DAC 210. The digital block baseline values in this example embodiment are integers selected to be approximately equal to lowest baseline carrier level in the corresponding block times a block scaling factor selected such that all of the digital block baseline values are in the input bit range of first stage DAC 210.

In this example embodiment, each digital pixel baseline difference value is an integer selected based on the lowest baseline carrier level in the corresponding block as well, or more specifically on the baseline carrier level of the corresponding capacitive sensing element minus the lowest baseline carrier level of the block. Each digital pixel baseline difference value is selected to be approximately equal to the baseline carrier level of the corresponding capacitive sensing element minus the lowest baseline carrier level in its block, then multiplied by a pixel scaling factor. It is noted that this example embodiment yields only positive digital pixel baseline difference values. Thus, both the input range and the output range of each second stage DAC 216 may be selected to allow only positive values.

Further, in this example embodiment, similarly to the previous example embodiment, the analog output range of first stage DAC 210 and the capacitance of block FPN DAC coupling capacitors 214 may be chosen such that there is a predetermined block FPN DAC gain between the lowest baseline carrier levels of each block and the corresponding block baseline voltage applied to summing junctions 208. Additionally, the analog output ranges of second stage DACs 216 and the capacitance of pixel FPN DAC coupling capacitors 220 may be chosen such that there is a predetermined pixel FPN DAC gain between the baseline carrier level of a capacitive sensing element minus the lowest baseline carrier level in its block and the corresponding pixel baseline voltage applied to summing junctions 208.

Although the calculations to determine the digital block baseline values and digital pixel baseline difference values are different in each of these examples, and therefore, the factors used to define the block and pixel FPN DAC gains are different, the results of each example may be similar. It is noted that in both of these examples, it is useful for the predetermined readout gain, the predetermined block FPN DAC gain, and predetermined pixel FPN DAC gain to be approximately equal.

Additionally, in both cases it may be useful for the output ranges of first stage DAC 210 and second stage DACs 216 to have approximately equal magnitudes (although in the first of these examples these ranges may be offset). The gains associated with the two DAC stages may then be scaled by selection of the capacitances of their respective coupling capacitors.

Figure 3:
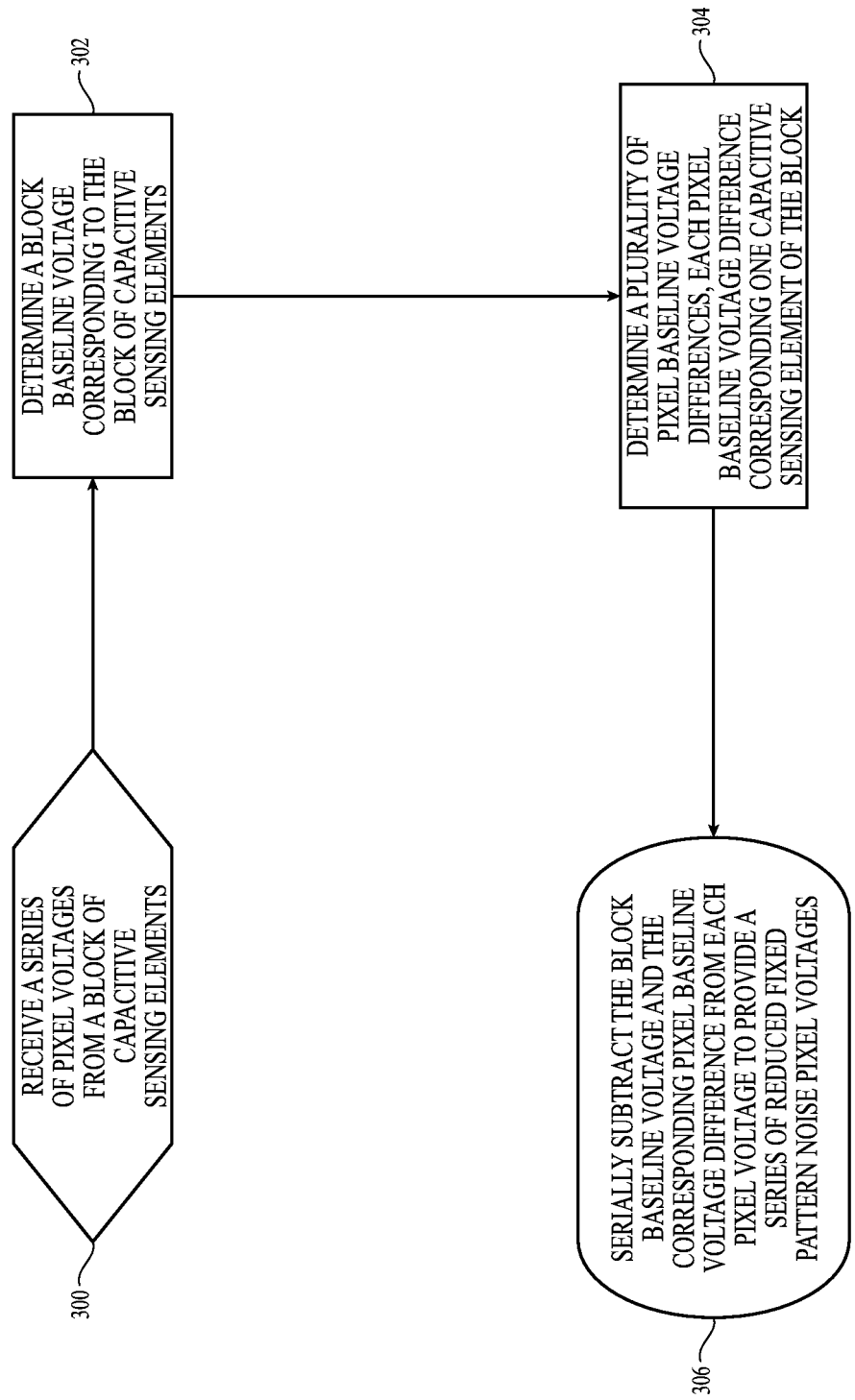
FIG. 3 is a flowchart illustrating an example FPN reduction method for pixel data from a block of a capacitive sensor array, as described herein.

FIG. 3 illustrates an example method for reducing FPN in a series of pixel voltages read out from a block of capacitive sensing elements. Although this example method may be performed using the example capacitive fingerprint sensor of FIG. 2, one skilled in the art may understand that this method may be used with other capacitive fingerprint sensor designs as well.

The series of pixel voltages is received, at step 300, for example by a summing junction as in the example embodiment of FIG. 2. In an example embodiment, receiving the series of pixel voltages may include separating the series of pixel voltages into subseries of pixel voltages corresponding to pixel voltages of column of the block of capacitive sensing elements. Each subseries of pixel voltages may be coupled to a corresponding summing junction.

A block baseline voltage corresponding to the block of capacitive sensing elements is determined at step 302. Pixel baseline voltage differences, one pixel baseline voltage difference corresponding to one capacitive sensing element of the block, are determined at step 304. As described above with reference to the example embodiment of FIG. 2, a number of methods may be used to determine these baseline voltages. For example, the block baseline voltage may be based the average baseline carrier level of the capacitive sensing elements in the block of capacitive sensing elements. It is noted that each pixel voltage of the series of pixel voltages is equal to the pixel charge of the corresponding capacitive sensing element times a predetermined gain factor. In this example embodiment, the block baseline voltage may be approximately equal to the average baseline carrier level of the block times the same predetermined gain factor. Further, determining the plurality of pixel baseline voltage differences begins with subtracting the average baseline carrier level from the baseline carrier level of each capacitive sensing element in the block to determine a baseline carrier difference for each capacitive sensing element. Each pixel baseline voltage difference may then be determined by multiplying a corresponding baseline carrier difference by the same predetermined gain factor used for the pixels voltages and the block baseline voltages to determine the plurality of pixel baseline voltage differences.

In another example, the block baseline voltage may be based the lowest baseline carrier level of the capacitive sensing elements in the block of capacitive sensing elements. In this example, the block baseline voltage may be approximately equal to the lowest baseline carrier level of the block times the predetermined gain factor. And the plurality of pixel baseline voltage differences may be determined by subtracting the lowest baseline carrier level from the baseline carrier level of each capacitive sensing element in the block to determine a baseline carrier difference for each capacitive sensing element, and then multiplying each baseline carrier difference by the gain factor to determine the plurality of pixel baseline voltage differences.

Once the block baseline voltage and the plurality of pixel baseline voltage differences have been determined, the block baseline voltage and the corresponding pixel baseline voltage difference are serially subtracted from each pixel voltage to provide a series of reduced FPN pixel voltages (step 306). It is noted that in the example embodiment described above in which the series of pixel voltages is separated into column subseries of pixel voltages before being coupled to separate summing junctions, each summing junction may produce a subseries of reduced FPN pixel voltages. In this example embodiment, the block baseline voltage may be generated using a block FPN DAC, as in the example embodiment of FIG. 2. The block baseline voltage may be coupled to each of the summing junctions. Subseries of pixel baseline voltage differences corresponding to each subseries of pixel voltages may be generated and coupled to the corresponding summing junction. Each of these subseries of pixel baseline voltage differences may be generated using a corresponding pixel FPN DAC as in the example embodiment of FIG. 2. Each summing junction may serially subtract the block baseline voltage and the corresponding pixel baseline voltage difference from each pixel voltage to provide a subseries of reduced FPN pixel voltages. The resulting subseries of reduced FPN pixel voltages may then be interleaved to provide the series of reduced FPN pixel voltages.

Figure 4:
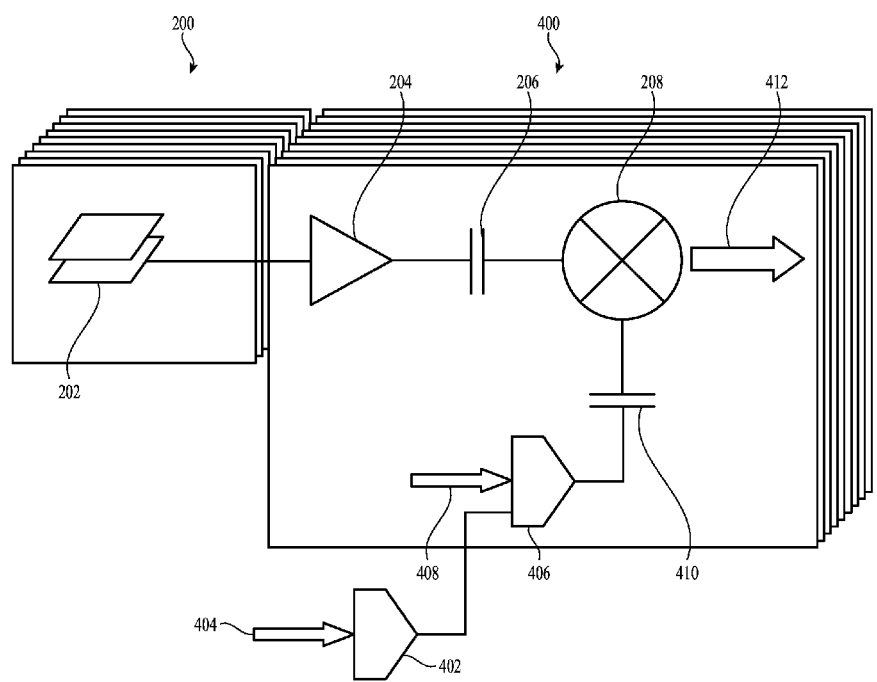
FIG. 4 is a schematic block diagram of an alternative example capacitive sensor array, readout circuitry and fixed pattern noise (FPN) reduction circuitry, as described herein, parallel processing lines are illustrated by stacked boxes.

FIG. 4 illustrates an alternative example capacitive fingerprint sensor. The example capacitive fingerprint sensor of FIG. 4 includes an array of capacitive sensing elements 202 (illustrated by row 200 of capacitive sensing elements 202, shown graphically by the stacked boxes of row 200, as in the example capacitive fingerprint sensor of FIG. 2), block FPN DAC 402, and parallel signal processing circuitry 400. As in the example embodiments of FIG. 2, the array of capacitive sensing elements include a number of blocks of capacitive sensing elements.

Readout circuitry (including preamplifier 204 and readout coupling capacitor 206) is electrically coupled to the array of capacitive sensing elements and is adapted to serially read out pixel charges from the capacitive sensing elements one row of one block at a time. As illustrated in FIG. 4, the readout circuitry may be separated into multiple parallel lines (shown graphically by the stacked boxes of parallel signal processing circuitry 400) each coupled to capacitive sensing elements of one column in each block.

As in the example embodiments of FIG. 2, block FPN DAC 402 is adapted to serially provide a block baseline carrier level for each block of the capacitive sensing elements based on block DAC input data 404. Block DAC input data 404 includes digital block baseline values corresponding to each block and a latching signal to synchronize the block FPN DAC 402 with the readout circuitry.

In this example embodiment, the output of block FPN DAC 402 is coupled to a number of pixel FPN DACs, each pixel FPN DAC corresponding to each parallel line of readout circuitry, i.e. each column of a block of capacitive sensing elements. Each pixel FPN DAC includes a second stage DAC 406 and a FPN DAC coupling capacitor 410. Each second stage DAC 406 receives the block baseline carrier levels from block FPN DAC 402 and is adapted to serially add, one row at a time, a pixel baseline carrier level difference for each capacitive sensing element of each block to the block baseline carrier level of the block to provide a pixel baseline carrier level for the corresponding capacitive sensing elements. Pixel DAC input data 408 includes a digital pixel baseline difference value approximately proportional to pixel baseline carrier level difference for each pixel in the corresponding column and a latching signal to synchronize the second stage DAC 406 with the readout circuitry.

It is noted that the digital block baseline values and the digital pixel baseline difference values may be determined using any of the methods described above.

Each summing junction 208 is capacitively coupled to the readout circuitry by readout coupling capacitor 206 to receive pixel voltages, which are proportional to the pixel charge of one capacitive sensing element. Each summing junction 208 is also capacitively coupled to one pixel FPN DAC by a corresponding FPN DAC coupling capacitor 410 to receive pixel baseline voltages. Thus, each pixel baseline voltage is proportional to the pixel baseline carrier level of a corresponding capacitive sensing element.

Each summing junction 208 is adapted to serially subtract the corresponding pixel baseline voltage from each pixel voltage to provide a subseries 412 of reduced FPN pixel voltages. Together these subseries 412 constitute a series of reduced FPN pixel voltages. Subseries 412 may be combined to produce a single series of reduced FPN pixel voltages for further signal processing as a single series or each subseries 412 may be processed further in parallel before being combined.

It should be appreciated that any signal paths discussed herein or shown in the corresponding figures may be differential or single-ended. Likewise, embodiments discussed herein may be implemented in any suitable silicon technology, including (but not limited to) CMOS, BICMOS, bipolar, high voltage, low voltage, and so forth.

While the present disclosure has been described with reference to various embodiments, it will be understood that these embodiments are illustrative and that the scope of the disclosure is not limited to them. Many variations, modifications, additions, and improvements are possible. More generally, embodiments in accordance with the present disclosure have been described in the context of particular embodiments. Functionality may be separated or combined in procedures differently in various embodiments of the disclosure or described with different terminology. These and other variations, modifications, additions, and improvements may fall within the scope of the disclosure as defined in the claims that follow.

The invention claimed is:

1. A capacitive fingerprint sensor, comprising:
an array of capacitive sensing elements, the array including a plurality of blocks of capacitive sensing elements;
readout circuitry electrically coupled to the array of capacitive sensing elements, the readout circuitry adapted to read out pixel voltages from a group of capacitive sensing elements of each block;
a first digital to analog converter (DAC) adapted to provide a block baseline voltage for each block of capacitive sensing elements, the baseline voltage corresponding to an accumulated charge in a given block in the absence of a finger;
at least one second DAC adapted to provide a pixel baseline voltage difference for one capacitive sensing element of each group of each block; and
at least one summing junction electrically coupled to the readout circuitry, the first DAC, and the at least one second DAC;
wherein the at least one summing junction is adapted to subtract the received block baseline voltage and the received pixel baseline voltage difference from the corresponding pixel voltage of each group of each block.

2. The capacitive fingerprint sensor of claim 1, wherein:
each block of the array of capacitive sensing elements has N rows and M columns of capacitive sensing elements, N and M being integers greater than one;
the groups of capacitive sensing elements readout of each block are the N rows;
the at least one second DAC is M second DACs, each second DAC adapted to provide a pixel baseline voltage difference for one capacitive sensing element of each row of each block; and
the at least one summing junction is M summing junctions.

3. The capacitive fingerprint sensor of claim 2, wherein N=M=9.

4. The capacitive fingerprint sensor of claim 2, wherein:
each capacitive sensing element of the array of capacitive sensing elements is adapted to store a pixel charge during a measurement period prior to read out;
the readout circuitry:
includes M parallel preamplifier stages and M readout coupling capacitors, each readout coupling capacitor coupled to one summing junction of M summing junctions; and
is adapted to:
read out the pixel charges from each block of capacitive sensing elements one row at a time;
provide one pixel charge from each row of each block to one parallel preamplifier stage to be amplified by the preamplifier stage; and
charge each readout coupling capacitor with the amplified pixel charges from one preamplifier stage to produce the pixel voltages.

5. The capacitive fingerprint sensor of claim 2, wherein:
the first DAC:
includes M first DAC coupling capacitors, each readout coupling capacitor coupled to one summing junction; and
is adapted to:
generate a block baseline charge for each block of the capacitive sensing elements based on a corresponding digital block baseline value; and
charge the M first DAC coupling capacitors with the block baseline charge to produce the block baseline voltages for each block of capacitive sensing elements; and
each second DAC includes a second DAC coupling capacitor coupled to the corresponding summing junction and is adapted to:

generate a pixel baseline charge difference for one capacitive sensing element in each row of each block based on a corresponding digital pixel baseline difference value; and charge the second DAC coupling capacitor with the pixel baseline charge difference to produce the pixel baseline voltage difference for the one capacitive sensing element.

6. The capacitive fingerprint sensor of claim 5, wherein:
the first DAC includes a G bit digital to analog converter, G being an integer greater than seven;
each digital block baseline value being an integer selected to be approximately equal to an average of baseline carrier levels of the capacitive sensing elements of the block times a block scaling factor, the block scaling factor selected such that every digital block baseline value is in a range from 0 to $2^G-1$;
the second DAC includes an H bit digital to analog converter, H being a positive integer less than seven;
each digital pixel baseline difference value being an integer selected to be approximately equal to the baseline carrier level of the capacitive sensing element minus the average of the baseline carrier levels of the capacitive sensing elements of the block, all times a pixel scaling factor, the pixel scaling factor selected such that every digital pixel baseline difference value is in a range from $-(2^H-1)/2$ to $(2^H-1)/2$.

7. The capacitive fingerprint sensor of claim 6, wherein G=9 and H=4.

8. The capacitive fingerprint sensor of claim 6, wherein:
each parallel preamplifier stage and corresponding readout coupling capacitor of the readout circuitry are selected such that the readout circuitry has a predetermined readout gain between pixel charge and pixel voltage;
the G bit digital to analog converter of the first DAC being adapted to generate block baseline charges in a range of 0 to a predetermined maximum block charge;
the G bit digital to analog converter and the M first DAC coupling capacitors of the first DAC are selected such that the first DAC has a predetermined first DAC gain between:
the average of the baseline carrier levels of the capacitive sensing elements of one block; and
the block baseline voltage for that block;
the H bit digital to analog converter of each second DAC being adapted to generate block baseline charges in a range of minus a predetermined maximum pixel charge to plus the predetermined maximum pixel charge;
the H bit digital to analog converter and the second DAC coupling capacitors of each second DAC are selected such that each second DAC has a predetermined second DAC gain between:
the baseline carrier level of one capacitive sensing element minus the average of the baseline carrier levels of the capacitive sensing elements of the block including the one capacitive sensing element; and
the pixel baseline voltage difference for that capacitive sensing element; and
the predetermined readout gain, the predetermined first DAC gain, and predetermined second DAC gain are approximately equal.

9. The capacitive fingerprint sensor of claim 8, wherein the predetermined maximum block charge of the G bit digital to analog converter of the first DAC is approximately equal to two times the predetermined maximum pixel charge of the H bit digital to analog converter of each second DAC.

10. The capacitive fingerprint sensor of claim 5, wherein:
the first DAC includes a G bit digital to analog converter, G being an integer greater than seven;
each digital block baseline value being an integer selected to be approximately equal to a lowest of baseline carrier levels of the capacitive sensing elements of the block times a block scaling factor, the block scaling factor selected such that every digital block baseline value is in a range from 0 to $2^G-1$;
the second DAC includes an H bit digital to analog converter, H being a positive integer less than seven;
each digital pixel baseline difference value being an integer selected to be approximately equal to the baseline carrier level of the capacitive sensing element minus the lowest of the baseline carrier levels of the capacitive sensing elements of the block, all times a pixel scaling factor, the pixel scaling factor selected such that every digital pixel baseline difference value is in a range from 0 to $2^H-1$.

11. The capacitive fingerprint sensor of claim 10, wherein G=9 and H=4.

12. The capacitive fingerprint sensor of claim 10, wherein:
each parallel preamplifier stage and corresponding readout coupling capacitor of the readout circuitry are selected such that the readout circuitry has a predetermined readout gain between pixel charge and pixel voltage;
the G bit digital to analog converter of the first DAC being adapted to generate block baseline charges in a range of 0 to a predetermined maximum block charge;
the G bit digital to analog converter and the M first DAC coupling capacitors of the first DAC are selected such that the first DAC has a predetermined first DAC gain between:
the lowest of the baseline carrier levels of the capacitive sensing elements of one block; and
the block baseline voltage for that block;
the H bit digital to analog converter of each second DAC being adapted to generate block baseline charges in a range of 0 to a predetermined maximum pixel charge;
the H bit digital to analog converter and the second DAC coupling capacitors of each second DAC are selected such that each second DAC has a predetermined second DAC gain between:
the baseline carrier level of one capacitive sensing element minus the lowest of the baseline carrier levels of the capacitive sensing elements of the block including the one capacitive sensing element; and
the pixel baseline voltage difference for that capacitive sensing element; and
the predetermined readout gain, the predetermined first DAC gain, and predetermined second DAC gain are approximately equal.

13. The capacitive fingerprint sensor of claim 12, wherein the predetermined maximum block charge of the G bit digital to analog converter of the first DAC is approximately equal to the predetermined maximum pixel charge of the H bit digital to analog converter of each second DAC.

14. A method for reducing fixed pattern noise (FPN) in a series of pixel voltages read out from a block of capacitive sensing elements in a fingerprint sensor, the method comprising:
receiving the series of pixel voltages from the block of capacitive sensing elements;
providing, by a first digital to analog converter (DAC), a block baseline voltage for the block of capacitive sensing elements, the block baseline voltage corresponding to an accumulated charge in the block in the absence of a finger;

providing, by a second DAC, a plurality of pixel baseline voltage differences, each pixel baseline voltage difference corresponding to one capacitive sensing element of the block;

serially subtracting, through a summing junction, the block baseline voltage and the corresponding pixel baseline voltage difference from each pixel voltage to provide a series of reduced FPN pixel voltages resulting in a fingerprint image.

15. The method of claim 14, wherein:

each pixel voltage of the series of pixel voltages is equal to a predetermined gain factor times a pixel charge of one capacitive sensing element of the block of capacitive sensing elements;

providing the block baseline voltage includes:
   determining an average baseline carrier level of the capacitive sensing elements in the block of capacitive sensing elements; and
   multiplying the average baseline carrier level by the gain factor to determine the block baseline voltage; and providing the plurality of pixel baseline voltage differences includes:
   subtracting the average baseline carrier level from the baseline carrier level of each capacitive sensing elements in the block of capacitive sensing elements to determine a baseline carrier difference for each capacitive sensing elements in the block of capacitive sensing elements; and
   multiplying each baseline carrier difference by the gain factor to determine the plurality of pixel baseline voltage differences.

16. The method of claim 14, wherein:

each pixel voltage of the series of pixel voltages is equal to a predetermined gain factor times a pixel charge of one capacitive sensing element of the block of capacitive sensing elements;

providing the block baseline voltage includes:
   determining a lowest baseline carrier level of a plurality of baseline carrier levels of capacitive sensing elements in the block of capacitive sensing elements; and
   multiplying the lowest baseline carrier level by the gain factor to determine the block baseline voltage; and providing the plurality of pixel baseline voltage differences includes:
   subtracting the average baseline carrier level from the baseline carrier level of each capacitive sensing elements in the block of capacitive sensing elements to determine a baseline carrier difference for each capacitive sensing elements in the block of capacitive sensing elements; and
   multiplying each baseline carrier difference by the gain factor to determine the plurality of pixel baseline voltage differences.

17. The method of claim 14, wherein:

the block of capacitive sensing elements includes N rows and M columns of capacitive sensing elements, N and M being integers greater than one;

receiving the series of pixel voltages from the block of capacitive sensing elements includes:
   separating the series of pixel voltages into M subseries of pixel voltages, each subseries corresponding to pixel voltages of column of the block of capacitive sensing elements; and
   coupling each subseries of pixel voltages to a corresponding summing junction of M summing junctions; and serially subtracting the block baseline voltage and the corresponding pixel baseline voltage difference from each pixel voltage to provide the series of reduced FPN pixel voltages includes:
   generating the block baseline voltage using the first DAC;
   coupling the block baseline voltage to each of the M summing junctions;
   generating subseries of pixel baseline voltage differences corresponding to each subseries of pixel voltages, each subseries of pixel baseline voltage differences generated using the second DAC of M second DACs;
   coupling each subseries of pixel baseline voltage differences to the corresponding summing junction of the M summing junctions;
   using each summing junction to serially subtract the block baseline voltage and the corresponding pixel baseline voltage difference from each pixel voltage to provide a subseries of reduced FPN pixel voltages;
   interleaving the M subseries of reduced FPN pixel voltages to provide the series of reduced FPN pixel voltages.

18. The method of claim 17, wherein M=N=8.

19. A capacitive fingerprint sensor, comprising:

an array of capacitive sensing elements, the array forming a plurality of blocks of capacitive sensing elements;

readout circuitry electrically coupled to the array of capacitive sensing elements, the readout circuitry adapted to serially read out pixel voltages from a group of capacitive sensing elements of each block;

a first digital to analog converter (DAC) adapted to provide a block baseline voltage for each block of capacitive sensing elements, the block baseline voltage corresponding to an accumulated charge in a given block in the absence of a finger;

at least one second DAC:
   coupled to the first DAC to serially receive the block baseline carrier levels; and
   adapted to serially add a pixel baseline carrier level difference for one capacitive sensing element of the group of each block to the block baseline carrier level of the block to generate a pixel baseline carrier level for the corresponding capacitive sensing element; and at least one summing junction each summing junction electrically coupled to:
   the readout circuitry to receive pixel voltages, each pixel voltage proportional to the pixel charge of one capacitive sensing element; and
   the at least one second DAC to receive pixel baseline voltages, each pixel baseline voltage proportional to the pixel baseline carrier level of one capacitive sensing element;

wherein the M summing junctions are adapted to serially subtract the corresponding pixel baseline voltage from each pixel voltage to provide a series of reduced fixed pattern noise (FPN) pixel voltages.

20. The capacitive fingerprint sensor of claim 19, wherein:

each block of the array of capacitive sensing elements includes N rows and M columns of capacitive sensing elements, N and M being integers greater than one;

the group of capacitive sensing elements is one row of the block;

the at least one second DAC is M second DACs, each second DAC adapted to serially add a pixel baseline carrier level difference for one capacitive sensing element of each row of each block to the block baseline carrier level of the block to generate a pixel baseline carrier level for the corresponding capacitive sensing element; and the at least one summing junction is M summing junctions.

21. The capacitive fingerprint sensor of claim 20, wherein:

the readout circuitry:
includes M column preamplifier stages and M readout coupling capacitors, each readout coupling capacitor coupled to one summing junction of M summing junctions; and
is adapted to:
read out the pixel charges from each block of capacitive sensing elements one row at a time;
provide pixel charges from each column of each block to a corresponding column preamplifier stage to be amplified; and
charge each readout coupling capacitor with the amplified pixel charges from one column preamplifier stage to produce M column subseries of pixel voltages;

the first DAC is adapted to:
generate a block baseline carrier level for each block of the capacitive sensing elements based on a corresponding digital block baseline value; and
provide the block baseline carrier level to each of the M FPN DACs; and each second DAC includes a second DAC coupling capacitor coupled to the corresponding summing junction and is adapted to:
serially generate a pixel baseline carrier level difference for capacitive sensing elements of one column of each block based on a corresponding digital pixel baseline difference value;
add each pixel baseline carrier level difference to the corresponding block baseline carrier level, to produce a pixel baseline carrier level; and
charge the second DAC coupling capacitor with the pixel baseline carrier level to produce a subseries of pixel baseline voltages for the one column of each block.

22. The capacitive fingerprint sensor of claim 21, wherein:

each digital block baseline value is an integer selected to be approximately equal to an average of baseline carrier levels of the capacitive sensing elements of the block times a block scaling factor; and each digital pixel baseline difference value is an integer selected to be approximately equal to the baseline carrier level of the capacitive sensing element minus the average of the baseline carrier levels of the capacitive sensing elements of the block, all times a pixel scaling factor.

23. The capacitive fingerprint sensor of claim 21, wherein:

each digital block baseline value is an integer selected to be approximately equal to a lowest baseline carrier level of baseline carrier levels of the capacitive sensing elements of the block times a block scaling factor; and each digital pixel baseline difference value is an integer selected to be approximately equal to the baseline carrier level of the capacitive sensing element minus the lowest baseline carrier level of the baseline carrier levels of the capacitive sensing elements of the block, all times a pixel scaling factor.

* * * * *